United States Patent
Ghosh et al.

(10) Patent No.: US 9,155,897 B2
(45) Date of Patent: Oct. 13, 2015

(54) CRITERIA FOR OPTIMAL ELECTRICAL RESYNCHRONIZATION DURING BIVENTRICULAR PACING

(71) Applicant: Medtronic, Inc., Minneapolis, MN (US)

(72) Inventors: Subham Ghosh, Circle Pines, MN (US); Robert W Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 2 days.

(21) Appl. No.: 13/886,884

(22) Filed: May 3, 2013

(65) Prior Publication Data
US 2014/0005740 A1     Jan. 2, 2014

Related U.S. Application Data
(60) Provisional application No. 61/642,754, filed on May 4, 2012.

(51) Int. Cl.
| | | |
|---|---|---|
| *A61N 1/37* | (2006.01) | |
| *A61B 5/0452* | (2006.01) | |
| *A61N 1/368* | (2006.01) | |

(52) U.S. Cl.
CPC ............ *A61N 1/3706* (2013.01); *A61B 5/0452* (2013.01); *A61N 1/3684* (2013.01); *A61N 1/3686* (2013.01); *A61N 1/3702* (2013.01)

(58) Field of Classification Search
CPC .......................... A61N 1/3686; A61N 1/3684
USPC .......................................................... 607/28
See application file for complete search history.

(56) References Cited

U.S. PATENT DOCUMENTS
| | | |
|---|---|---|
| 4,497,326 A | 2/1985 | Curry |
| 4,940,052 A | 7/1990 | Mann et al. |

(Continued)

FOREIGN PATENT DOCUMENTS
| | | |
|---|---|---|
| WO | WO 2005/089867 A1 | 9/2005 |
| WO | WO 2013/123340 A2 | 8/2013 |

(Continued)

OTHER PUBLICATIONS
International Search Report and Written Opinion for PCT patent application PCT/US2013/026425, Jun. 4, 2013, 8 pgs.

(Continued)

*Primary Examiner* — Michael Kahelin
(74) *Attorney, Agent, or Firm* — Carol F. Barry

(57) ABSTRACT

Generally, the disclosure is directed one or more methods or systems of cardiac pacing employing a right ventricular electrode and a plurality of left ventricular electrodes. Pacing using the right ventricular electrode and a first one of the left ventricular electrodes and measuring activation times at other ones of the left ventricular electrodes. Pacing using the right ventricular electrode and a second one of the ventricular electrodes and measuring activation times at other ones of the left ventricular electrodes. Computing a first degree of resynchronization based on a sum of differences of activation times and corresponding activation times. Pacing using the right ventricular electrode and a second one of the ventricular electrodes and measuring activation times at other ones of the left ventricular electrodes. Computing a second degree of resynchronization based on the sum of differences of activation times and corresponding activation times. Selecting one of the left ventricular electrodes for delivery of subsequent pacing pulses based on the computed degrees of resynchronization.

3 Claims, 9 Drawing Sheets

(56) References Cited

U.S. PATENT DOCUMENTS

| | | |
|---|---|---|
| 5,443,492 A | 8/1995 | Stokes et al. |
| 5,628,778 A | 5/1997 | Kruse et al. |
| 5,922,014 A | 7/1999 | Warman et al. |
| 6,236,883 B1 | 5/2001 | Ciaccio et al. |
| 6,606,516 B2 | 8/2003 | Levine |
| 6,795,732 B2 | 9/2004 | Stadler et al. |
| 6,804,555 B2 | 10/2004 | Warkentin |
| 6,968,237 B2 | 11/2005 | Doan et al. |
| 7,031,777 B2 | 4/2006 | Hine et al. |
| 7,142,919 B2 | 11/2006 | Hine et al. |
| 7,181,284 B2 | 2/2007 | Burnes et al. |
| 7,225,014 B1 | 5/2007 | Province |
| 7,239,913 B2 | 7/2007 | Ding et al. |
| 7,289,850 B2 | 10/2007 | Burnes et al. |
| 7,313,444 B2 | 12/2007 | Pianca et al. |
| 7,590,446 B1 | 9/2009 | Min et al. |
| 7,637,867 B2 | 12/2009 | Zdeblick |
| 7,702,390 B1 | 4/2010 | Min |
| 7,787,951 B1 | 8/2010 | Min |
| 7,860,580 B2 | 12/2010 | Falk et al. |
| 7,917,214 B1 | 3/2011 | Gill et al. |
| 7,941,217 B1 | 5/2011 | Pei et al. |
| 8,010,194 B2 | 8/2011 | Muller |
| 8,036,743 B2 | 10/2011 | Savage et al. |
| 8,126,552 B2 | 2/2012 | Min |
| 8,145,308 B2 | 3/2012 | Sambelashvili et al. |
| 8,155,739 B2 | 4/2012 | Keel et al. |
| 8,160,700 B1 | 4/2012 | Ryu et al. |
| 8,175,707 B1 | 5/2012 | Wright et al. |
| 8,615,298 B2 | 12/2013 | Ghosh et al. |
| 8,620,433 B2 | 12/2013 | Ghosh et al. |
| 2003/0100925 A1 | 5/2003 | Pape et al. |
| 2004/0106958 A1 | 6/2004 | Mathis et al. |
| 2005/0038478 A1 | 2/2005 | Klepfer et al. |
| 2005/0125041 A1 | 6/2005 | Min et al. |
| 2005/0149138 A1 | 7/2005 | Min et al. |
| 2006/0235478 A1 | 10/2006 | Van Gelder et al. |
| 2007/0129762 A1 | 6/2007 | Worley |
| 2008/0058656 A1 | 3/2008 | Costello et al. |
| 2008/0294218 A1 | 11/2008 | Savage et al. |
| 2008/0306567 A1 | 12/2008 | Park et al. |
| 2009/0036947 A1 | 2/2009 | Westlund et al. |
| 2009/0054941 A1 | 2/2009 | Eggen et al. |
| 2009/0254140 A1 | 10/2009 | Rosenberg et al. |
| 2009/0270729 A1 | 10/2009 | Corbucci et al. |
| 2009/0299423 A1 | 12/2009 | Min |
| 2010/0016914 A1 | 1/2010 | Mullen et al. |
| 2010/0121397 A1 | 5/2010 | Cholette |
| 2010/0145405 A1 | 6/2010 | Min et al. |
| 2010/0152801 A1 | 6/2010 | Koh et al. |
| 2010/0204593 A1 | 8/2010 | Park et al. |
| 2010/0262204 A1 | 10/2010 | McCabe et al. |
| 2010/0268059 A1 | 10/2010 | Ryu et al. |
| 2011/0022110 A1 | 1/2011 | Min |
| 2011/0022112 A1 | 1/2011 | Min |
| 2011/0066201 A1 | 3/2011 | Rosenberg et al. |
| 2011/0066202 A1 | 3/2011 | Rosenberg et al. |
| 2011/0066203 A1 | 3/2011 | Rosenberg et al. |
| 2011/0098770 A1 | 4/2011 | Ryu et al. |
| 2011/0098772 A1 | 4/2011 | Min |
| 2011/0118803 A1 | 5/2011 | Hou et al. |
| 2011/0137369 A1 | 6/2011 | Ryu et al. |
| 2011/0257697 A1 | 10/2011 | Jarverud |
| 2011/0319953 A1 | 12/2011 | Reed et al. |
| 2011/0319954 A1 | 12/2011 | Niazi et al. |
| 2012/0004700 A1 | 1/2012 | Hedberg et al. |
| 2012/0239116 A1 | 9/2012 | Lee et al. |
| 2012/0296387 A1 | 11/2012 | Zhang et al. |
| 2013/0190834 A1 | 7/2013 | Ghosh et al. |
| 2013/0218223 A1 | 8/2013 | Ghosh et al. |
| 2013/0218224 A1 | 8/2013 | Ghosh et al. |
| 2013/0218225 A1 | 8/2013 | Ghosh et al. |
| 2013/0218226 A1 | 8/2013 | Ghosh et al. |
| 2013/0218227 A1 | 8/2013 | Ghosh et al. |
| 2014/0236252 A1 | 8/2014 | Ghosh et al. |
| 2014/0236253 A1 | 8/2014 | Ghosh et al. |
| 2015/0045849 A1 | 2/2015 | Ghosh et al. |

FOREIGN PATENT DOCUMENTS

| | | |
|---|---|---|
| WO | WO 2013/123367 A1 | 8/2013 |
| WO | WO 2013/123386 A1 | 8/2013 |

OTHER PUBLICATIONS

International Search Report and Written Opinion for PCT patent application PCT/US2013/026399, Jun. 19, 2013, 10 pgs.

International Search Report and Written Opinion for PCT patent application PCT/US2013/026366, Sep. 5, 2013, 9 pgs.

CRITERIA FOR OPTIMAL ELECTRICAL RESYNCHRONIZATION DURING BIVENTRICULAR PACING

CROSS-REFERENCE TO RELATED APPLICATIONS

This application claims the benefit of U.S. Provisional Application No. 61/642,754, filed on May 4, 2012. The disclosure of the above application is incorporated herein by reference in its entirety.

FIELD

The present disclosure relates to implantable medical devices (IMDs), and, more particularly, to selecting an optimal left ventricular electrode on a medical electrical lead extending from an IMD to deliver cardiac therapy delivery.

BACKGROUND

Implantable medical devices (IMD) are capable of utilizing pacing therapies, such as cardiac resynchronization therapy (CRT), to maintain hemodynamic benefits to patients. Pacing therapy may be delivered from an implantable generator, through a lead, and into the patient's heart. There are many ways in which to optimize a pacing configuration. CRT therapy involves biventricular pacing which consists of pacing the right ventricle (RV) with a RV electrode and a left ventricle (LV) with a LV electrode or monoventricular pacing which consists of pacing only the left ventricle. US Patent Publication 2011/0137639 by Ryu et al. discloses that the optimal left ventricle electrode is selected based upon conduction velocities. Another U.S. Pat. No. 7,917,214 to Gill et al. discloses that the optimal left ventricle electrode is selected based upon activation times and ARI dispersions. It is desirable to develop additional methods to optimize biventricular pacing.

DETAILED DESCRIPTION OF EXEMPLARY EMBODIMENTS

Figure 1:
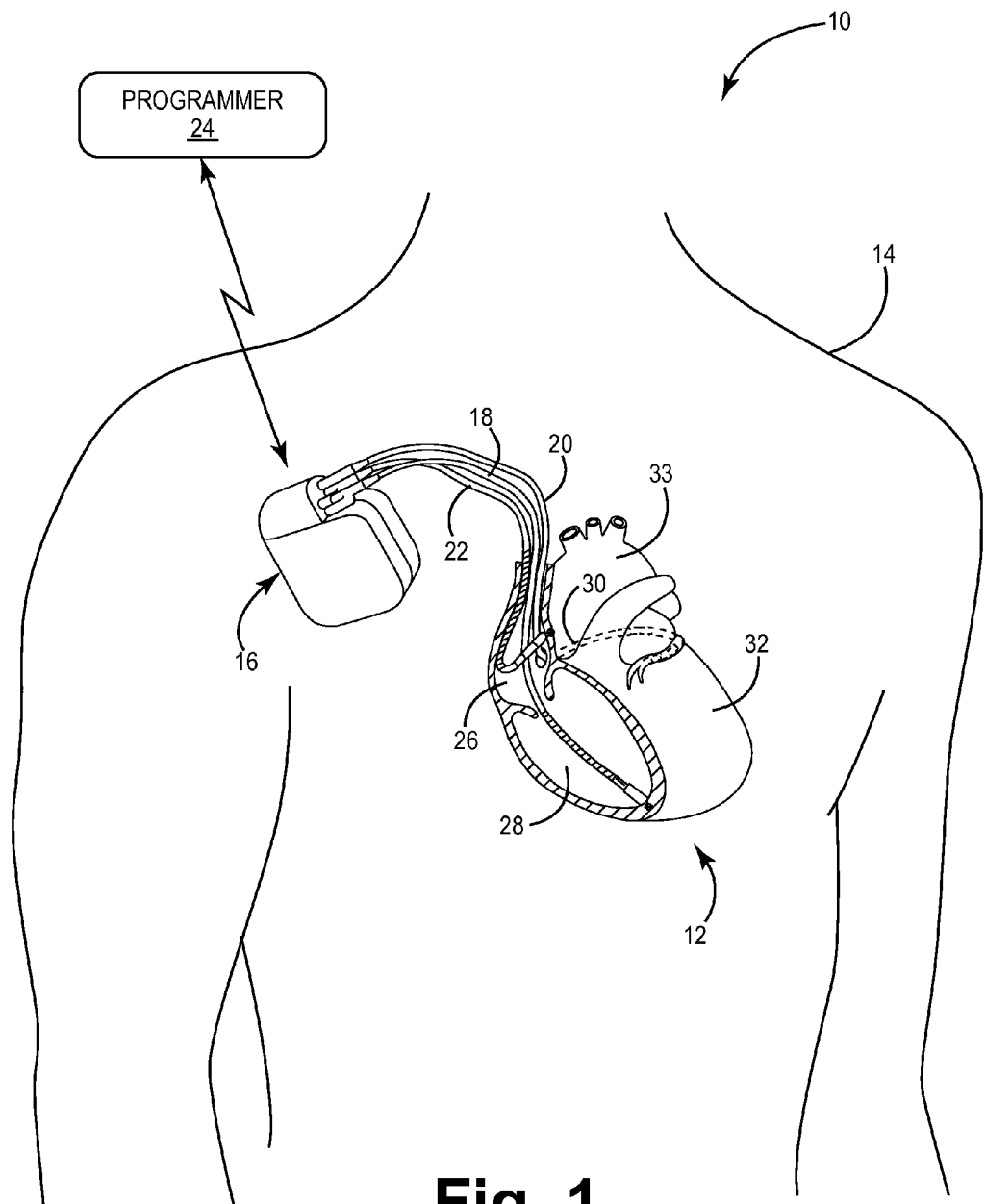
FIG. 1 is a schematic diagram of an exemplary system including an exemplary implantable medical device (IMD).

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

As described herein, a physician implanting a medical device can use criteria, stored in a programmer, to automatically select optimized location(s) and/or parameters for delivery of cardiac resynchronization therapy (CRT). For example, criteria can be used to determine an optimal left ventricular electrode from which electrical stimuli is delivered to the left ventricle. After the optimal LV electrode has been selected, other criteria can be used to optimize an atrioventricular delay, and/or an inter-ventricular delay for maximal cardiac resynchronization. Implementation of teachings of this disclosure can potentially improve CRT response in patients.

Exemplary methods, devices, and systems are described with reference to FIGS. 1-8. It is appreciated that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

FIG. 1 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22 and a programmer 24. For the sake of brevity, programmer 24 includes a computer capable of the functions represented in FIG. 4 that are incorporated herein.

The IMD 16 may be, e.g., an implantable pacemaker, cardioverter, and/or defibrillator, that provides electrical signals to the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular coronary sinus lead 20 extends through one or more veins, the vena cava, the right atrium 26, and into the coronary sinus 30 to a region adjacent to the free wall of the left ventricle (LV) 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., pulse width, amplitude, voltage, burst length, etc. Further, the IMD 16 may be operable to use various electrode configurations to deliver pacing therapy, which may be unipolar or bipolar. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

In some examples, a programmer 24, which may be a handheld computing device or a computer workstation, may be used by a user, such as a physician, technician, another clinician, and/or patient, to communicate with the IMD 16 (e.g., to program the IMD 16). For example, the user may interact with the programmer 24 to retrieve information concerning one or more detected or indicated faults associated within the IMD 16 and/or the pacing therapy delivered therewith. The IMD 16 and the programmer 24 may communicate via wireless communication using any techniques known in the art. Examples of communication techniques may include, e.g., low frequency or radiofrequency (RF) telemetry, but other techniques are also contemplated.

Figure 2:
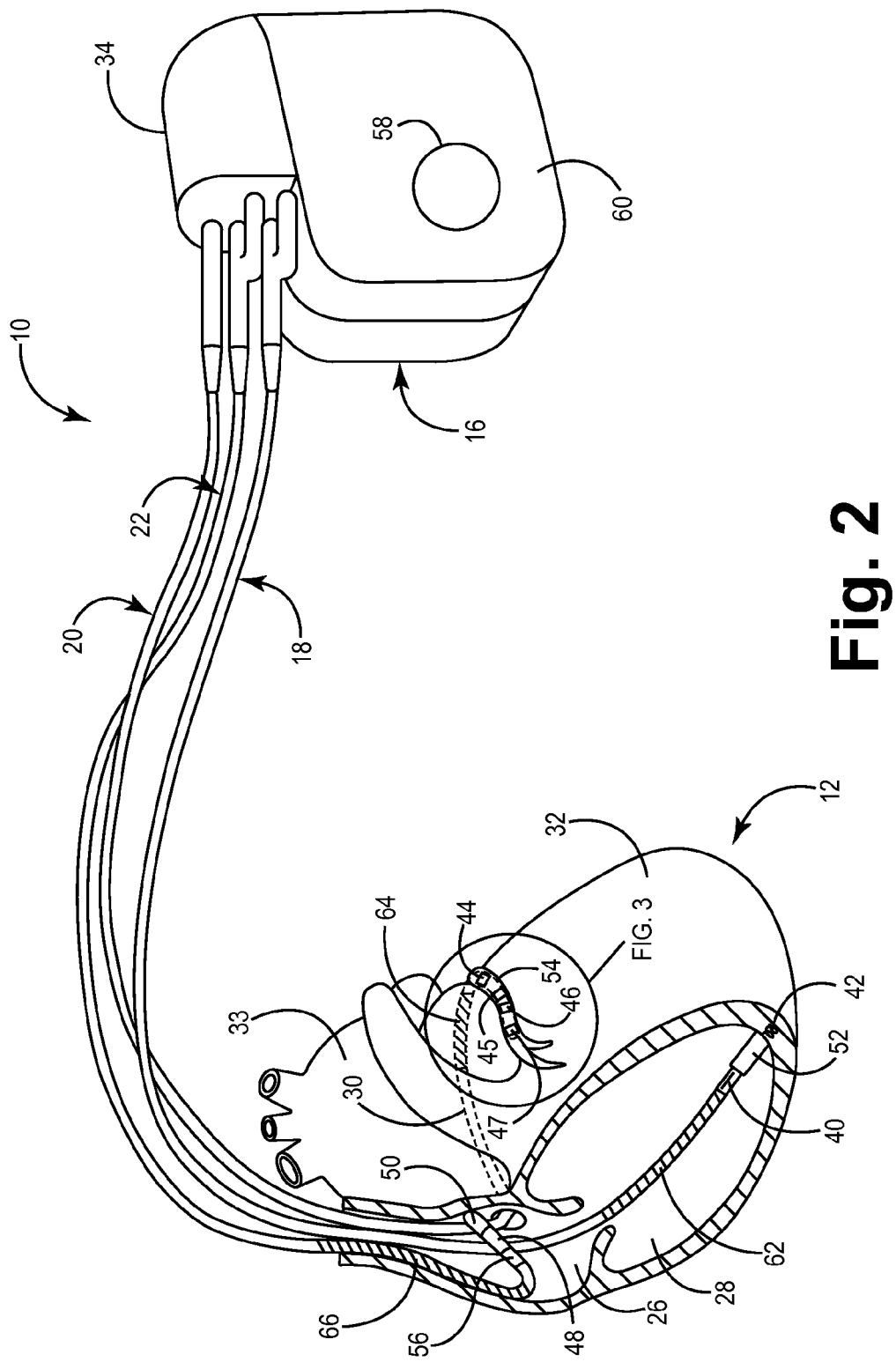
FIG. 2 is a schematic diagram of the exemplary IMD of FIG. 1.

FIG. 2 is a conceptual diagram illustrating the IMD 16 and the leads 18, 20, 22 of therapy system 10 of FIG. 1 in more detail. The leads 18, 20, 22 may be electrically coupled to a therapy delivery module (e.g., for delivery of pacing therapy), a sensing module (e.g., one or more electrodes to sense or monitor electrical activity of the heart 12 for use in determining effectiveness of pacing therapy), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths).

Exemplary leads that can be useful for the present disclosure include U.S. Pat. No. 5,922,014, U.S. Pat. No. 5,628,778, U.S. Pat. Nos. 4,497,326, 5,443,492, U.S. Pat. No. 7,860,580 or US Patent Application 20090036947 filed Apr. 30, 2008 such that electrodes are added and/or spaced apart in a manner similar to that disclosed in the figures of the present application, all of listed patents and applications are incorporated by reference in their entirety. Additional lead and electrode configurations that may be adapted for use with the present disclosure by adjusting lead shape, length, electrode number and/or electrode to effectively avoid phrenic nerve stimulation as described herein are generally disclosed in U.S. Pat. No. 7,031,777, U.S. Pat. No. 6,968,237, and US Publication No. 2009/0270729, all of which are incorporated herein by reference in their entirety. Moreover, U.S. Pat. No. 7,313,444, incorporated by reference, discloses a LV pacing lead such that the LV electrodes are about equally spaced, which could also be used to implement the present disclosure.

Figure 3:
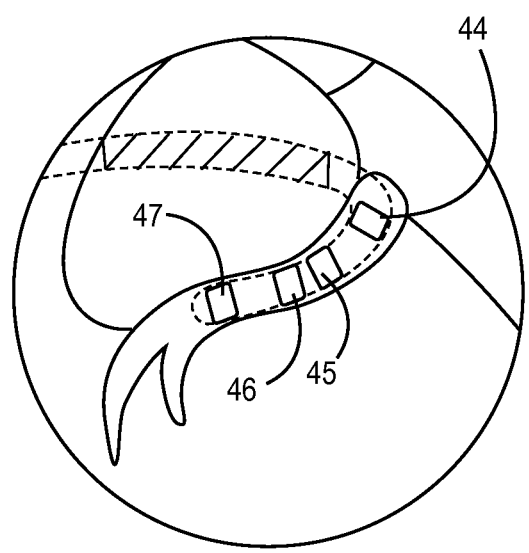
FIG. 3-3A are schematic diagrams of an enlarged view of a distal end of a medical electrical lead disposed in the left ventricle.
Figure 3A:
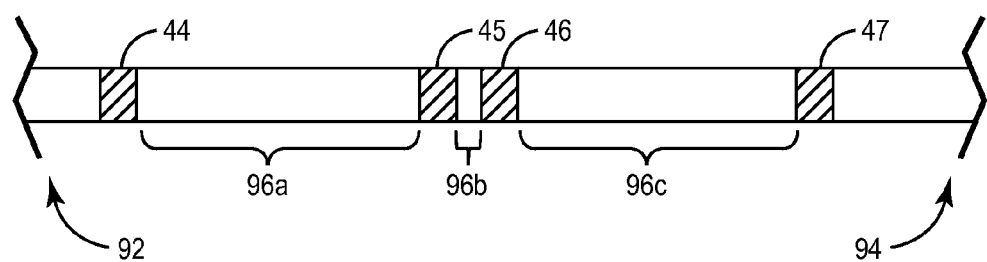

In the illustrated example, bipolar or unipolar electrodes 40, 42 (also referred to as RV electrodes) are located proximate to a distal end of the lead 18. Referring briefly to FIGS. 3-3A, the electrodes 44, 45, 46 are located proximate to a distal end of the lead 20 and the bipolar or unipolar electrodes 56, 50 (FIG. 2) are located proximate to a distal end of the lead 22. Electrodes 44, 45, 46 and 47 can be bipolar electrodes, unipolar electrodes or a combination of bipolar and unipolar electrodes. Additionally, electrodes 44, 45, 46 and 47 have an electrode surface area of about 5.3 mm² to about 5.8 mm². Electrodes 44, 45, 46, and 47 are also referred to as LV1 (electrode 1), LV2 (electrode 2), LV3 (electrode 3), and LV4 (electrode 4), respectively. As shown, lead 20 includes a proximal end 92 and a distal end 94. The distal end 94 is placed in or near LV tissue. Skilled artisans appreciate that LV electrodes (i.e. left ventricle electrode 1 (LV1) 44, left ventricle electrode 2 (LV2) 45, left ventricle electrode 3 (LV3) 46, and left ventricle 4 (LV4) 47 etc.) on lead 20 can be spaced apart at variable distances. For example, electrode 44 is a distance 96a (e.g. about 21 mm) away from electrode 45, electrodes 45 and 46 are spaced a distance 96b (e.g. about 1.3 mm to about 1.5 mm) away from each other, and electrodes 46 and 47 are spaced a distance 96c (e.g. 20 mm to about 21 mm) away from each other.

The electrodes 40, 44, 45, 46, 47, 48 may take the form of ring electrodes, and the electrodes 42, 47, 50 may take the form of extendible helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to respective ones of the electrical contacts on the proximal end of the leads 18, 20, 22. The electrodes 40, 42, 44, 45, 46, 47, 48, 50 may further be used to sense electrical signals attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 2, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48 and 50 may be used for unipolar sensing or pacing in combination with housing electrode 58. Further, any of electrodes 40, 42, 44, 45, 46, 47, 48, 50, 58, which are not being used to deliver pacing therapy, may be used to sense electrical activity during pacing therapy (e.g., for use in determining electrical activation times). Electrical activation time can be used to determine whether pacing (e.g. LV only pacing or biventricular pacing) produces effective contraction of the heart based on metrics of degree of resynchronization derived from the ventricular activation times.

Electrical activation time or local electrical activity is determined relative to timing of a fiducial, an indicator of a global cardiac event (e.g. timing of contraction of a chamber of the heart, timing of pacing of a chamber of the heart, etc.) For example, the fiducial may be the onset of QRS, the peak of QRS (e.g. minimum values, minimum slopes, maximum slopes), zero crossings, threshold crossings, etc. of a near or far-field EGM), onset of application of a pacing electrical stimulus, or the like. After a fiducial point is selected, activation times are determined by measuring time between the delivery of pacing stimulus using a pacing electrode and the appropriate fiducial point with the electrical activity sensed by a non-pacing electrode. The timing may be the initiation of the pacing signal or the like. The device delivering the pacing signal may include appropriate electronics to track and mark the timing of the pacing signal, which marked or tracked time may be used for purposes of determining local activation time and electrical dispersion as discussed above. The device that delivers the pacing signal may be a device configured for delivering CRT.

As described in further detail with reference to FIG. 4, the housing 60 may enclose a therapy delivery module that may include a stimulation generator for generating cardiac pacing pulses and defibrillation or cardioversion shocks, as well as a sensing module for monitoring the patient's heart rhythm. Cardiac pacing involves delivering electrical pacing pulses to the patient's heart, e.g., to maintain the patient's heart beat (e.g., to regulate a patient's heart beat, to improve and/or maintain a patient's hemodynamic efficiency, etc.). Cardiac pacing involves delivering electrical pacing pulses ranging from about 0.25 volts to about 8 volts and more preferably, between 2-3 volts.

The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity during pacing therapy (e.g., for use in determining activation times). In at least one embodiment, the LV elongated electrode 64 may be used to sense electrical activity of a patient's heart during the delivery of pacing therapy. Electrodes used to sense a response from cardiac tissue are transmitted to an A/D converter to convert the analog signal to a digital signal. The digital signal is then transmitted to the microprocessor 80. The microprocessor 80 determines the level of response sensed at a particular electrode.

The configuration of the exemplary therapy system 10 illustrated in FIGS. 1-2 is merely one example. In other examples, the therapy system may include epicardial leads and/or patch electrodes instead of or in addition to the transvenous leads 18, 20, 22 illustrated in FIG. 1. Further, in one or more embodiments, the IMD 16 need not be implanted within the patient 14. For example, the IMD 16 may deliver defibrillation shocks and other therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. Other examples of therapy systems may include three transvenous leads located as illustrated in FIGS. 1-3. Still further, other therapy systems may include a single lead that extends from the IMD 16 into the right atrium 26 or the right ventricle 28, or two leads that extend into a respective one of the right atrium 26 and the right ventricle 28.

Figure 4:
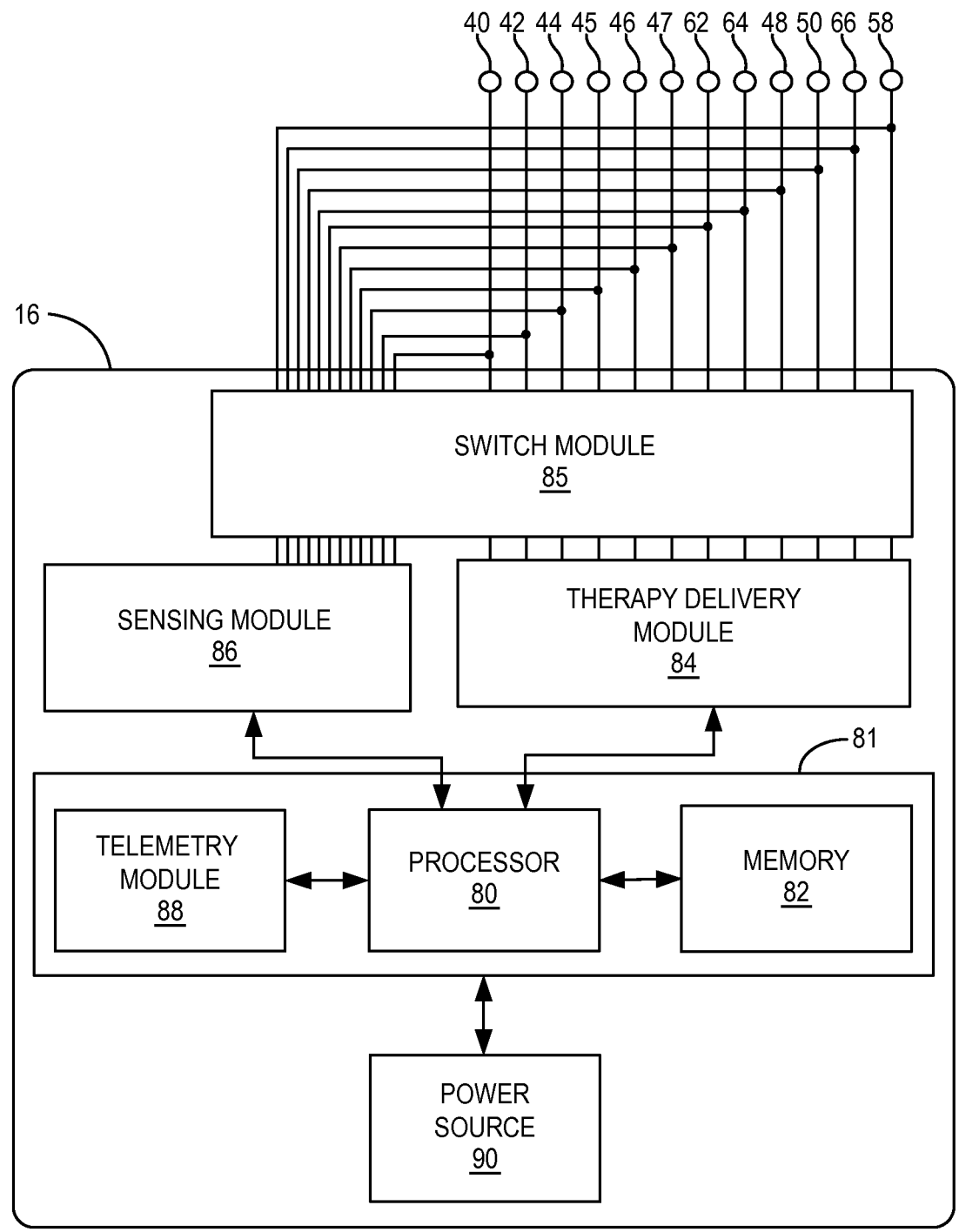
FIG. 4 is a block diagram of an exemplary IMD, e.g., the IMD of FIGS. 1-2.

FIG. 4 is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control the therapy delivery module 84 to deliver electrical stimulus such as, e.g., pacing pulses with the amplitudes, pulse widths, frequency, or electrode polarities specified by the selected one or more therapy programs (e.g., pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 48 coupled to leads 18, 20, and 22, respectively, and/or helical tip electrodes 42, 46, and 50 of leads 18, 20, and 22, respectively. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to monitor heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may also be used with the sensing module 86 to select which of the available electrodes are used, e.g. to sense electrical activity of the patient's heart. In some examples, the control module 81 may select the electrodes that function as sensing electrodes via the switch module within the sensing module 86, e.g., by providing signals via a data/address bus. In some examples, the sensing module 86 may include one or more sensing channels, each of which may include an amplifier.

In some examples, sensing module 86 includes a channel that includes an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter (ND) for storage in memory 82 as an electrogram (EGM). In some examples, the storage of such EGMs in memory 82 may be under the control of a direct memory access circuit. The control module 81 (e.g., using the processor 80) may employ digital signal analysis techniques to characterize the digitized signals stored in memory 82 to detect and classify the patient's heart rhythm from the electrical signals. For example, the processor 80 may be configured to measure activation times of cardiac tissue using EGMs from one or more electrodes in contact, or in proximity, with cardiac tissue by employing any of the numerous signal processing methodologies known in the art.

If IMD 16 is configured to generate and deliver pacing pulses to the heart 12, the control module 81 may include a pacer timing and control module, which may be embodied as hardware, firmware, software, or any combination thereof. The pacer timing and control module may include one or more dedicated hardware circuits, such as an ASIC, separate from the processor 80, such as a microprocessor, and/or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module within control module 81 may include atrial and ventricular pacing escape intervals, refractory periods during which sensed P-waves and R-waves are ineffective to restart timing of the escape intervals, and/or the pulse widths of the pacing pulses. As another example, the pacer timing and control module may define a blanking period, and provide signals from sensing module 86 to blank one or more channels, e.g., amplifiers, for a period during and after delivery of electrical stimulation to the heart 12. The durations of these intervals may be determined in response to stored data in memory 82. The pacer timing and control module of the control module 81 may also determine the amplitude of the cardiac pacing pulses.

During pacing, escape interval counters within the pacer timing/control module may be reset upon sensing of R-waves and P-waves. Therapy delivery module 84 (e.g., including a stimulation generator) may include one or more pacing output circuits that are coupled, e.g., selectively by the switch module 85, to any combination of electrodes 40, 42, 44, 45, 46, 47, 48, 50, 58, 62, or 66 appropriate for delivery of a bipolar or unipolar pacing pulse to one of the chambers of heart 12. The control module 81 may reset the escape interval counters upon the generation of pacing pulses by therapy delivery module 84, and thereby control the basic timing of cardiac pacing functions, including anti-tachyarrhythmia pacing.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as the programmer 24 as described herein with respect to FIG. 1. For example, under the control of the processor 80, the telemetry module 88 may receive downlink telemetry from and send uplink telemetry to the programmer 24 with the aid of an antenna, which may be internal and/or external. The processor 80 may provide the data to be uplinked to the programmer 24 and the control signals for the telemetry circuit within the telemetry module 88, e.g., via an address/data bus. In some examples, the telemetry module 88 may provide received data to the processor 80 via a multiplexer. In at least one embodiment, the telemetry module 88 may be configured to transmit an alarm, or alert, if the pacing therapy becomes ineffective or less effective.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

After the LV lead 20 has been properly positioned on or near the LV tissue, schematically shown in FIG. 3, a variety of pacing configurations (e.g. biventricular pacing configurations, LV only pacing etc.) can be tested. Data generated from each pacing configuration can be useful in determining the optimal LV electrode from which to pace the LV. Biventricular pacing configurations are defined by a RV electrode pacing the RV while one or more LV electrodes pace the LV. Each biventricular configuration employs a different LV electrode (e.g. LV1, LV2, LV3, and LV4 etc.) for pacing.

Exemplary methods and/or devices described herein evaluate the effectiveness of pacing based on metrics of degree of resynchronization derived from the measured cardiac electrical activation times for each biventricular pacing configuration employing a different LV electrode. FIGS. 5-8 flow diagrams present different exemplary methods for selecting an optimal LV electrode.

Figure 5:
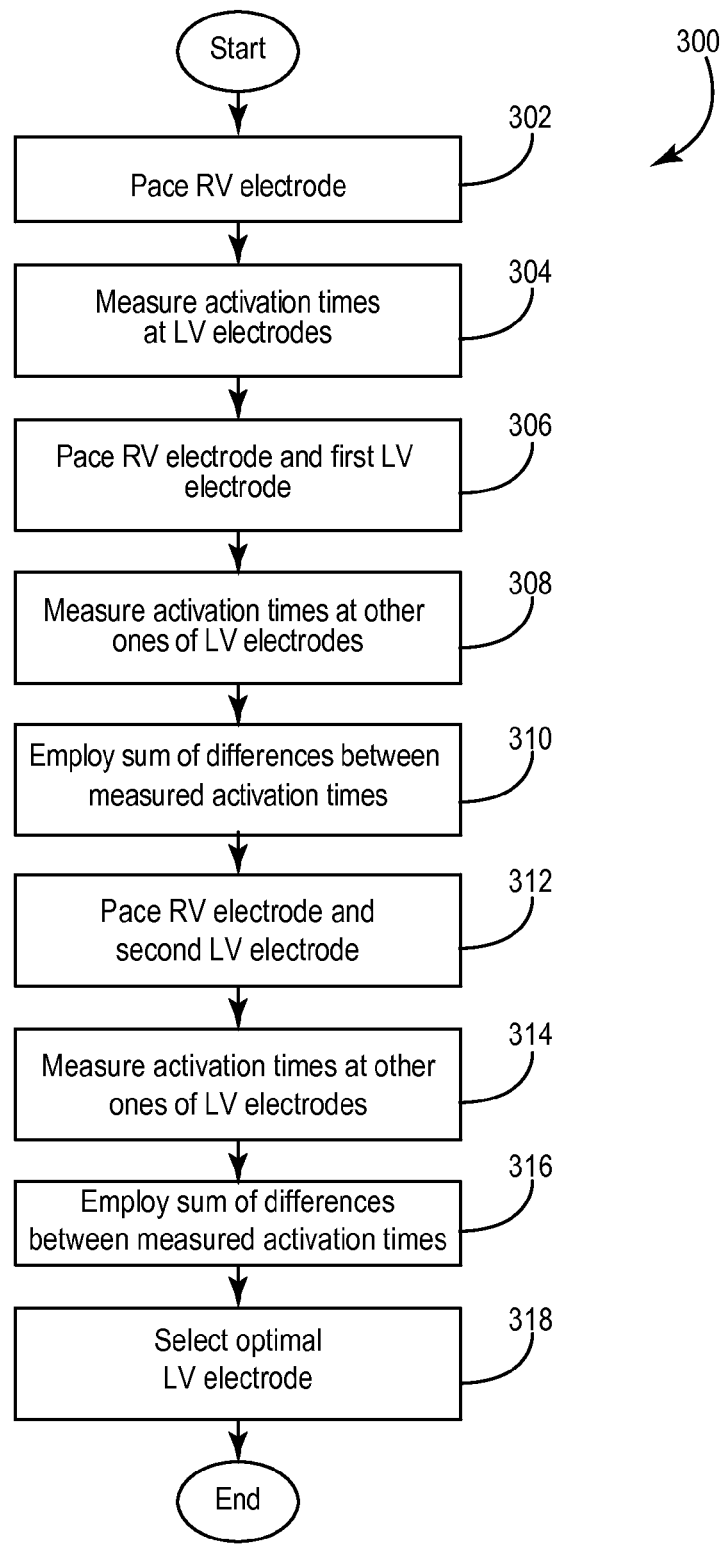
FIG. 5 is another general flow chart of an exemplary method that relies on a degree of resynchronization for selecting an optimal left ventricle electrode to pace a left ventricle.

FIG. 5 is a flow diagram that depicts a method 300 in which the optimal LV electrode is selected from which to pace the LV. Generally, the optimal LV electrode is selected based upon a comparison of degrees of resynchronization achieved for each LV electrode. Degree of resynchronization is a sum of differences between measured electrical activation times determined during RV only pacing (also referred to as a baseline) and biventricular pacing. The following example shows a sum of differences between measured electrical activation times measured during RV only pacing (also referred to as a baseline) and biventricular pacing in order to select the optimal LV electrode from which to pace the LV. The programmer 24 can be configured to pace only from the RV electrode and measure activation times at each of the electrodes during RV only pacing at operation 302. The electrical activation times are acquired at electrodes LV1, LV2, LV3 and LV4 during RV only pacing respectively at operation 304. The user or programmer 24 can then begin to test different biventricular pacing configurations by automatically or manually selecting the RV electrode and one of the LV electrodes to pace. In one or more embodiments, pacing pulses are delivered through the RV electrode and the LV electrode at a constant nominal A-V delay (e.g. 50 ms) and a nominal V-V delay (e.g. 0 ms). The first biventricular configuration involves delivering pacing pulses through the RV electrode to the RV and the LV1 (referred to as the first LV electrode) to the LV at block 306. The electrical activations times at LV2-LV4 electrodes are determined at block 308. The LV electrode used for pacing may not sense an activation time; therefore, no activation time is available for that electrode The degree of resynchronization is then determined as the sum of the activation time differences at operation 310. In this particular case, the degree of resynchronization is computed as follows:
(activation time at LV2 during RV only pacing−activation time at LV2 during biventricular pacing from RV electrode and LV1)+(activation time at LV3 during RV only pacing−activation time at LV3 during biventricular pacing from RV electrode and LV1)+(activation time at LV4 during RV only pacing−activation time at LV4 during biventricular pacing from RV electrode and LV1). The data generated by delivering pacing pulses from the RV and LV1 electrodes and the degree of resynchronization are stored into memory 82.
The user or programmer 24 then selects yet another biventricular configuration that paces a different LV electrode (also referred to as the second LV electrode) to test at block 312. For example, the second biventricular configuration includes LV2 that can be used to pace the LV while the RV electrode delivers pacing pulses to the RV at block 312. After a certain amount of time, the electrical activation times for the LV1, LV3 and LV4 are measured and stored into memory. The activation times for LV1, LV3, and LV4, are determined respectively at block 314.

At block 316, the degree of resynchronization is then determined by taking the sum of differences between measured activation times, as shown below:
(activation time at LV1 during RV only pacing−activation time at LV1 during biventricular pacing from RV electrode and LV2)+(activation time at LV3 during RV only pacing−activation time at LV3 during biventricular pacing from RV electrode and LV2)+(activation time at LV4 during RV only pacing−activation time at LV4 during biventricular pacing from RV electrode and LV2). The data generated by delivering pacing pulses from the RV and LV2 electrodes and the degree of resynchronization are stored into memory 82.

A third biventricular pacing configuration is then tested. The third biventricular pacing configuration includes the RV electrode and the LV3 that deliver pacing pulses to the RV and LV, respectively. The programmer 24, therefore, switches from LV2 to LV3 to deliver the pacing pulses to the LV. After the programmer 24 has selected the LV3, pacing pulses are delivered to the RV and LV through the RV and LV3 electrodes, respectively. After a certain amount of time, the electrical activation times for the LV1, LV2, and LV4 are determined and stored into memory 82. The degree of resynchronization is determined as follows:
(activation time at LV1 during RV only pacing−activation time at LV1 during biventricular pacing from RV electrode and LV3)+(activation time at LV2 during RV only pacing−activation time at LV2 during biventricular pacing from RV electrode and LV3)+(activation time at LV4 during RV only pacing−activation time at LV4 during biventricular pacing from RV electrode and LV3). The data generated by delivering pacing pulses through the RV and LV3 electrodes and the degree of resynchronization are stored into memory 82.

A fourth biventricular pacing configuration is then tested. The fourth biventricular pacing configuration includes the RV electrode and the LV4 that deliver pacing pulses to the RV and LV, respectively. The programmer 24 switches from LV3 to LV4 to deliver the pacing pulses to the LV. After the programmer 24 has selected LV4, pacing pulses are delivered to the RV and LV through the RV and LV4 electrodes, respectively. After a certain amount of time, the electrical activation times for the LV1, LV2, and LV3 are determined and stored into memory. The degree of resynchronization is determined as follows:
(activation time at LV1 during RV only pacing−activation time at LV1 during biventricular pacing from RV electrode and LV4)+(activation time at LV2 during RV only pacing−activation time at LV2 during biventricular pacing from RV electrode and LV4)+(activation time at LV3 during RV only pacing−activation time at LV3 during biventricular pacing from RV electrode and LV4). The data generated by delivering pacing pulses from the RV and LV4 electrodes and the degree of resynchronization are stored into memory.

It can be appreciated by the skilled artisan the number of disparate LV pacing electrodes may be less than 4 or may exceed 4, depending on number of available poles or electrodes in a multipolar lead and based on the separation between the electrodes. Two electrodes are considered to be disparate if the separation between them exceeds or equals 5 mm. In another embodiment similar determination of degree of resynchronization may be performed for each of the available LV electrodes by employing sum of differences of activation times between LV only pacing (instead of biventricular pacing) and RV only pacing.

The LV electrodes with a degree of resynchronization less than a certain threshold value (40 ms) will not be considered. If the degrees of resynchronization for all available LV electrodes do not exceed this threshold, then the RV and/or LV leads will be repositioned and the degrees of resynchronization for the new lead position(s) would be determined. For each of the LV electrodes with degree of resynchronization above threshold, a relative degree of resynchronization will be determined as the degree of resynchronization divided by the sum of the baseline (RV only pacing) activation times measured at other LV electrodes (excluding the electrode in question) multiplied by 100 (expressed as a percentage). The relative degree of resynchronization will help eliminate possible bias towards electrodes which have earlier activation times during baseline or RV only pacing. All electrode(s) which have a relative degree of resynchronization within 10% of the maximum relative degree of resynchronization are assumed to provide equivalent benefit and would be candidate electrodes for resynchronization therapy. The final electrode for cardiac resynchronization will be chosen from among these electrodes by giving consideration to other non-degree of resynchronization factors. Non-degree of resynchronization factors include activation times during intrinsic or RV only pacing (the latest electrode among the candidate electrode will be chosen), evidence of phrenic nerve stimulation during implant, battery life, etc. Detection of phrenic nerve stimulation may be accomplished by, for example, techniques described in US20120296387 A1 to Zhang et al. which is incorporated herein in its entirety. Four examples are provided below to illustrate how candidate electrodes may be chosen in different scenarios for the quadripolar lead described earlier where electrodes LV2 and LV3 are close together (1.5 mm separation) while electrodes 1 and 4 are roughly equidistant from them. In this case, since electrodes LV 2 and LV3 are very close to each other, LV 2 and LV3 considered as one [LV(2, 3)] electrode and their activation times are averaged:

Example 1

Normal Substrate

Normal Substrate is electrically viable tissue such as tissue without scars. In this example, activation times at electrodes LV1, LV(2, 3) and LV4 during RV only pacing are 105 ms, 90 ms and 75 ms, respectively. Activation times during biventricular pacing from RV and LV1 at electrodes LV (2, 3) and LV (4) are 10 ms and 20 ms respectively. Therefore, the degree of resynchronization for LV1 is (90−10)+(75−20)=135 ms. Since degree of resynchronization exceeds the threshold of 40 ms, a relative degree of resynchronization for LV1 is determined as a percentage of the baseline (i.e. RV only pacing) activation times=135/(90+75)*100=82%. Activation-times during biventricular pacing from electrode RV and LV(2, 3) measured at electrodes LV1 and LV4 are 10 and 10 respectively. The degree of resynchronization for LV (2, 3) is (105−10)+(75−10)=160 ms which exceeds the threshold of 40 ms. Therefore the relative degree of resynchronization for LV(2, 3) is also determined as 160/(105+75)*100=89%. Activation-times during biventricular pacing from electrode RV and LV4 at electrodes LV1 and LV(2, 3) are 20 ms and 10 ms respectively. Therefore, the degree of resynchronization for electrode LV4 is (105−20)+(90−10)=165 ms which exceeds the threshold of 40 ms. Therefore, a relative degree of resynchronization for electrode LV4 is 165/(105+90)*100=85%. The electrode LV(2, 3) has maximum relative degree of resynchronization, which is 89%. All electrodes with relative degree of resynchronization greater than or equal to 89−10=79% should be candidate electrodes for resynchronization pacing. In this example, all LV electrodes satisfy this criteria and one of them should be chosen for the final therapy based on non-degree of resynchronization factors.

Example 2

Conduction Delay of 90 ms Due to Anatomic Block (i.e. Scar) Between Electrodes LV(2, 3) and 1

Activation times during baseline RV only pacing at electrodes 1, (2, 3) and 4 are 180 ms, 90 ms and 75 ms respectively. Activation times during biventricular pacing from RV and LV1 at electrodes LV (2, 3) and LV (4) are 90 ms and 100 ms respectively. Therefore the degree of resynchronization for LV1 is (90−90)+(75−100)=−25 ms which is lower than the threshold of 40 ms. Therefore, electrode LV1 is eliminated as a possible electrode to pace the LV. Activation-times during biventricular pacing from electrode RV and LV(2, 3) measured at electrodes LV1 and LV4 are 90 and 10 respectively. The degree of resynchronization for LV (2, 3) is (180−90)+(75−10)=155 ms which exceeds the threshold of 40 ms. Therefore the relative degree of resynchronization for LV(2, 3) is determined as 155/(180+75)*100=61%, Activation-times during biventricular pacing from electrode RV and LV4 at electrodes LV1 and LV(2, 3) are 100 ms and 10 ms respectively. Therefore, the degree of resynchronization for electrode LV4 is (180−100)+(90−10)=160 ms which exceeds the threshold of 40 ms. Therefore, a relative degree of resynchronization for electrode LV4 is 160/(180+90)*100=59%. The electrode LV(2, 3) has maximum relative degree of resynchronization, which is 61%. All electrodes with relative degree of resynchronization greater than or equal to 61−10=51% should be candidate electrodes for resynchronization pacing. In this example, electrodes LV (4) and LV(2, 3) satisfy this criteria and one of them should be chosen for the final therapy based on non-degree of resynchronization factors.

Example 3

Lack of Enough Separation Between RV Electrode and LV Lead

Activation times during baseline RV only pacing at electrodes 1, (2, 3) and 4 are 20 ms, 10 ms and 20 ms respectively. Activation times during biventricular pacing from RV and LV1 at electrodes LV (2, 3) and LV (4) are 10 ms and 20 ms respectively. Therefore, the degree of resynchronization for LV1 is (10−10)+(20−20)=0 ms, which is lower than the threshold of 40 ms. Consequently, electrode LV1 is ruled out for pacing. Activation-times during biventricular pacing from electrode RV and LV(2, 3) measured at electrodes LV1 and LV4 are 10 and 10 respectively. The degree of resynchronization for LV (2, 3) is (20−10)+(20−10)=10 ms which is less than the threshold of 40 ms. Electrode LV (2, 3) is ruled out as well. Activation-times during biventricular pacing from electrode RV and LV4 at electrodes LV1 and LV(2, 3) are 20 ms and 10 ms respectively. The degree of resynchronization for electrode LV4 is (20−20)+(10−10)=0 ms which is less than the threshold of 40 ms. Therefore electrode LV4 is ruled out as well. Hence, all available electrodes are eliminated and, in this case, the recommended action would be to reposition RV and/or LV leads for achieving greater degrees of resynchronization. The recommended action is displayed on the graphical user interface of programmer 24.

Example 4

LV Lead in a Complicated Substrate with Scar/Fibrosis Comprising of Functional and Anatomic Blocks which Delay Conduction Activation times during baseline RV only pacing at electrodes 1, (2, 3) and 4 are 150 ms, 180 ms and 200 ms respectively. Activation times during biventricular pacing from RV and LV1 at electrodes LV (2, 3) and LV (4) are 170 ms and 190 ms respectively. Therefore, the degree of resynchronization for LV1 is (180−170)+(200−190)=10 ms, which is lower than the threshold of 40 ms. Therefore, electrode LV1 is ruled out for pacing. Activation-times during biventricular pacing from electrode RV and LV(2, 3) measured at electrodes LV1 and LV4 are 160 and 210 ms respectively. The degree of resynchronization for LV (2, 3) is (150−160)+(200−210)=−20 ms which is less than the threshold of 40 ms. Therefore, electrode LV (2, 3) is ruled out as well. Activation-times during biventricular pacing from electrode RV and LV4 at electrodes LV1 and LV(2, 3) are 150 ms and 190 ms respectively. Therefore, the degree of resynchronization for electrode LV4 is (150−150)+(180−190)=−10 ms which is less than the threshold of 40 ms. Therefore electrode LV4 is ruled out as well. Hence all available electrodes are ruled out and in this case the recommended action would be to reposition RV and/or LV leads for more separation and achieving greater degrees of resynchronization.

If the degree of resynchronization does not exceed the threshold value for all available LV electrodes, the recommendation of which lead to reposition may be provided by tracking the latest activation times recorded at an LV electrode during RV only pacing. If this latest time is less than a certain value (e.g. 60 ms), then the RV lead is the recommended lead to reposition. If the latest activation time recorded at an LV electrode during RV only pacing exceeds this value, then the LV lead is probably in a bad spot and needs to be repositioned.

Figure 6:
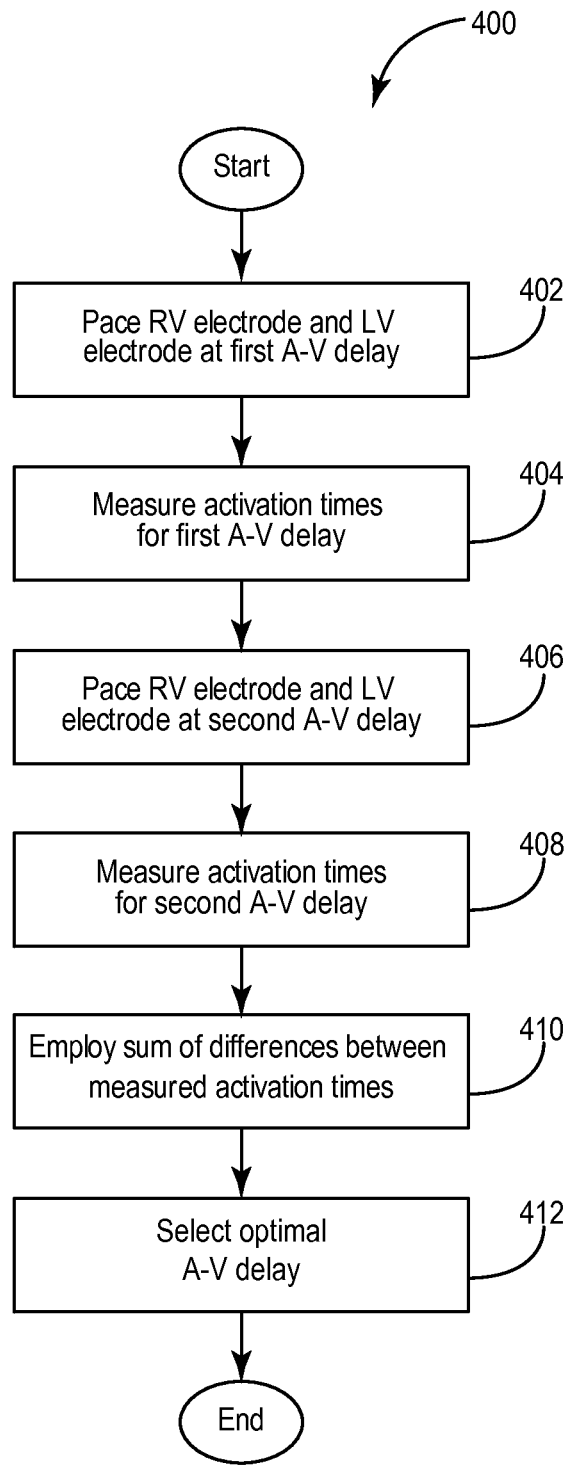
FIG. 6 is another general flow chart of an exemplary method that relies on a degree of resynchronization for selecting an optimal A-V delay.

After the optimal LV electrode has been selected, the optimal A-V delay can be selected through method 400 shown and described relative to FIG. 6. The A-V example begins at operation 402 in which the RV and LV electrodes (or only the LV electrode in cases where resynchronization is being delivered by LV only pacing) are paced using a first A-V delay during atrial sensing or atrial pacing. Activation times are determined at the disparate non-pacing LV electrodes by the processor at operation 404. At operation 406, the RV and LV electrode are paced using a second A-V delay. Activation times are measured at the disparate non-pacing LV electrodes \at operation 408. The definition of a disparate non-pacing electrode is an electrode which is located at a distance equal to or greater than 5 mm from a pacing electrode.

At operation 410, a sum of differences between measured activation times is determined for the first A-V delay. The degree of resynchronization is then determined as follows: (activation time at LV1 during RV only pacing−activation time at LV1 during biventricular pacing from RV electrode and LV3)+(activation time at LV2 during RV only pacing−activation time at LV2 during biventricular pacing from RV electrode and LV3)+(activation time at LV4 during RV only pacing−activation time at LV4 during biventricular pacing from RV electrode and LV3). The data generated by delivering pacing pulses from the RV and LV3 electrodes and the degree of resynchronization are stored into memory 82.

The programmer 24 can automatically pace an optimal LV electrode that can be evaluated at a baseline (i.e. resting heart rate) compared to a variety of sensed A-V delays while determining degrees of resynchronization associated with each A-V delay. The variety of A-V delays are tested starting from a short sensed A-V delay (e.g. 40 ms) that is gradually incremented (e.g. 20 ms) until a maximum or upper limit (e.g. 240 ms) is reached.

An optimal sensed A-V delay is determined based through sorting each of the degree of resynchronization and then programmer 24 selecting a maximum degree of resynchronization among all of the tested A-V delays at operation 412. If two or more sensed A-V delay have the same maximum degree of resynchronization, the shortest A-V delay of the two or more A-V delays are selected for the final CRT. The same operation may be performed during atrial pacing for paced A-V delays to find the optimal paced A-V delay at the baseline (resting) heart rate. $\Delta AVrest$ is determined by taking the difference between the resting optimal paced A-V delay and optimal sensed A-V delay. $\Delta AVrest$ is then stored in memory. The programmer 24 can evaluate optimal paced AV delays at different heart rates above the resting heart rate by performing atrial pacing at increased rates until a programmed upper tracking rate, and determining the corresponding optimal paced A-V delay. The corresponding optimal sensed A-V delay may be determined by subtracting $\Delta AVrest$ from the optimal paced A-V delay. The optimal sensed and paced A-V delays for different heart rates may be stored in the device in the form of a look-up table which can be used to dynamically adapt the sensed or paced A-V delay in response to changing heart rates.

A look-up table can be generated of optimal PAV and SAV values for different cycle-lengths that can be used for optimal and dynamic adaptation of A-V delay corresponding to different sensed or paced cycle-lengths. In particular, A-V optimization can automatically adjust A-V delays according to changes in heart rates (e.g. faster heart or lower cycle-lengths). The programmer 24 or IMD 16 can adjust the AV delay by using the look-up table that relates cycle length, PAV and/or SAV. For example, the IMD 16 can easily adjust the AV delay (whether atrial-sensed or atrial-paced) according to the detected current cycle-length. Accordingly, the PAV can be adjusted or the SAV can be adjusted to the designated optimum levels.

To generate a lookup table, programmer 24, for example, can initiate atrial pacing at different rates. The optimal PAV can be determined and stored into memory for a given atrial pacing rate. The corresponding optimal SAV can be determined for the same rate by subtracting $\Delta AV_{rest}$ as previously discussed and storing the optimal SAV value for that rate.

After A-V delay has been optimized, the V-V delay undergoes the optimization process. V-V optimization occurs in a similar manner as that which was performed to select the optimal LV electrode from which to pace. In one or more embodiments, V-V optimization can be performed through a use of a weighted sum of activation times for various V-V delays and the V-V that results in the lowest activation time is selected and programmed into the programmer 24.

In order to determine the optimal V-V delay, an degree of resynchronization must be calculated for two or more V-V delays with the A-V delay set to optimal value $A_{opt}$.

Table 1 summarizes degrees of resynchronization (in ms) with variable sensed A-V delays (in ms) during pacing from the RV electrode and pacing from the optimal LV electrode (i.e. electrode 3). In this case, the maximum degree of resynchronization is 165 ms, which occurs at two A-V delays of 140 ms and 160 ms respectively. The shorter A-V delay of these two A-V delays, 140 ms, would be selected as the optimal A-V delay. Table 1 summarizes A-V delays and the degree of resynchronization associated with each A-V delay.

TABLE 1

Selection of sensed A-V delay based on Degrees of Resynchronization

| A_V | 40 | 60 | 80 | 100 | 120 | 140 | 160 | 180 | 200 | 220 | 240 |
|---|---|---|---|---|---|---|---|---|---|---|---|
| Degree Of Resynchronization | 130 | 145 | 145 | 150 | 150 | 165 | 165 | 155 | 130 | 80 | −20 |

Figure 7:
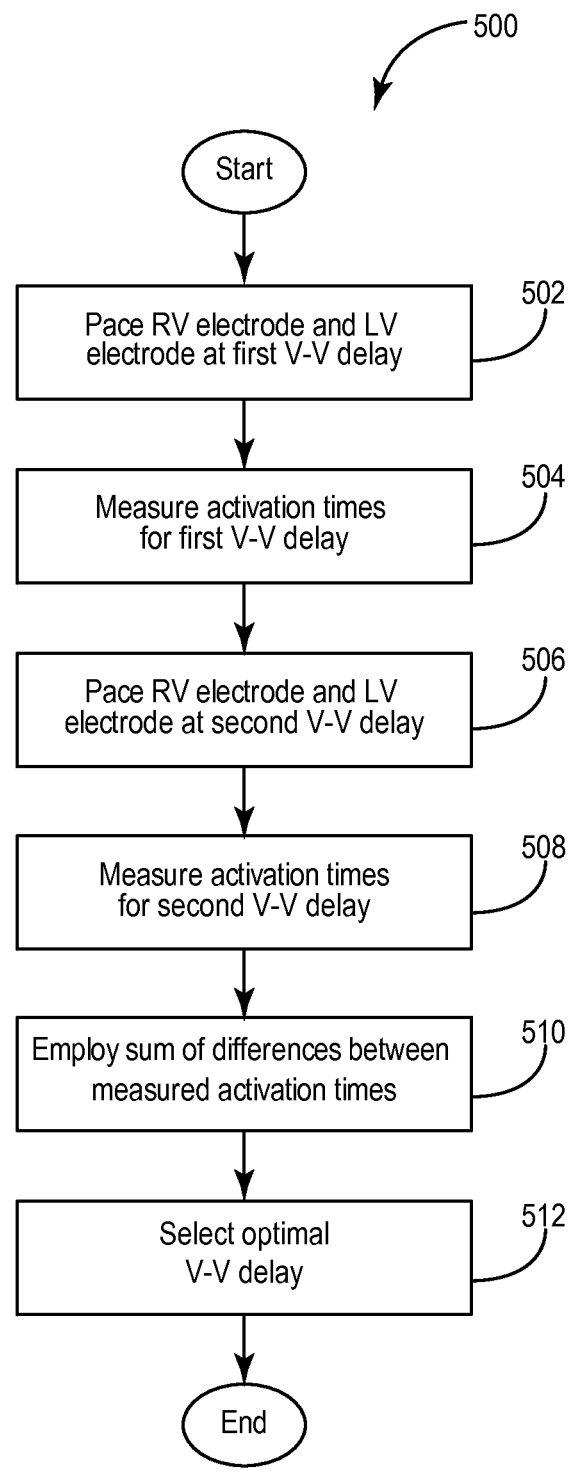
FIG. 7 is another general flow chart of an exemplary method that relies on a degree of resynchronization for selecting an optimal V-V delay.

After the optimal A-V delay has been selected, the optimal V-V delay can be selected through method 500 shown and described relative to FIG. 7. The V-V example begins at operation 502 in which the RV and LV electrodes are paced using a first V-V delay. Activation times are sensed at the non-pacing LV electrodes (LV1, LV2 and LV4) and measured at the processor at operation 504. At operation 506, the RV and LV electrode are paced using a second V-V delay. Activation times are measured at the non-pacing LV electrodes (LV1, LV2 and LV4) at operation 508. At operation 510, a sum of differences between measured activation times is determined for the first V-V delay. The degree of resynchronization is then determined as follows:
(activation time at LV1 during RV only pacing−activation time at LV1 during biventricular pacing from RV electrode and LV3)+(activation time at LV2 during RV only pacing−activation time at LV2 during biventricular pacing from RV electrode and LV3)+(activation time at LV4 during RV only pacing−activation time at LV4 during biventricular pacing from RV electrode and LV3). The data generated by delivering pacing pulses from the RV and LV3 electrodes and the degree of resynchronization are stored into memory 82.

The optimal V-V delay is determined based on maximum degree of resynchronization at operation 512. In this case, the optimal V-V delay is at 0 ms, since it produces a greater degree of resynchronization compared to other values of V-V delays. When two V-V delays produces equal degrees of resynchronization the V-V delay which has a lower magnitude would be selected as the optimal V-V delay.

Table 2 summarizes degrees of resynchronization (in ms) with variable A-V delays (in ms) during pacing from the RV electrode and pacing from the optimal LV electrode (i.e. electrode 3). In particular, the programmer 24 may automatically introduce variable V-V delays between the RV electrode and the LV electrode 3, from −50 ms to +50 ms, and determine the degree of resynchronization.

Table 2 summarizes V-V delays and the degree of resynchronization associated with each V-V delay.

TABLE 2

Biventricular pacing data using a set of V-V delays

| A-V | −50 | −40 | −30 | −20 | −10 | 0 | 10 | 20 | 30 | 40 | 50 |
|---|---|---|---|---|---|---|---|---|---|---|---|
| Degree of Resynchronization | −10 | 8 | −10 | 80 | 150 | 165 | 150 | 66 | 40 | −30 | −50 |

One or more embodiments relate to employing the degree of resynchronization to determine whether RV/LV leads 18, 20 should be repositioned. Repositioning of the RV lead 18 and/or the LV lead 20 is advisable after determining that biventricular or left ventricular only pacing fails to achieve adequate improvement over RV only pacing. Preferably, the RV lead 18 is repositioned before considering whether the LV lead 20 should be moved since the RV lead 18 is easier for a physician to move within the heart cavity.

Skilled artisans appreciate that when delivering CRT, which employs biventricular pacing, the pacing RV electrode 40, 42 must be spaced apart from the pacing LV electrode. If the RV and LV pacing electrodes are too close together, biventricular pacing provides little or no augmentative effect on resynchronization compared to RV only pacing.

Figure 8:
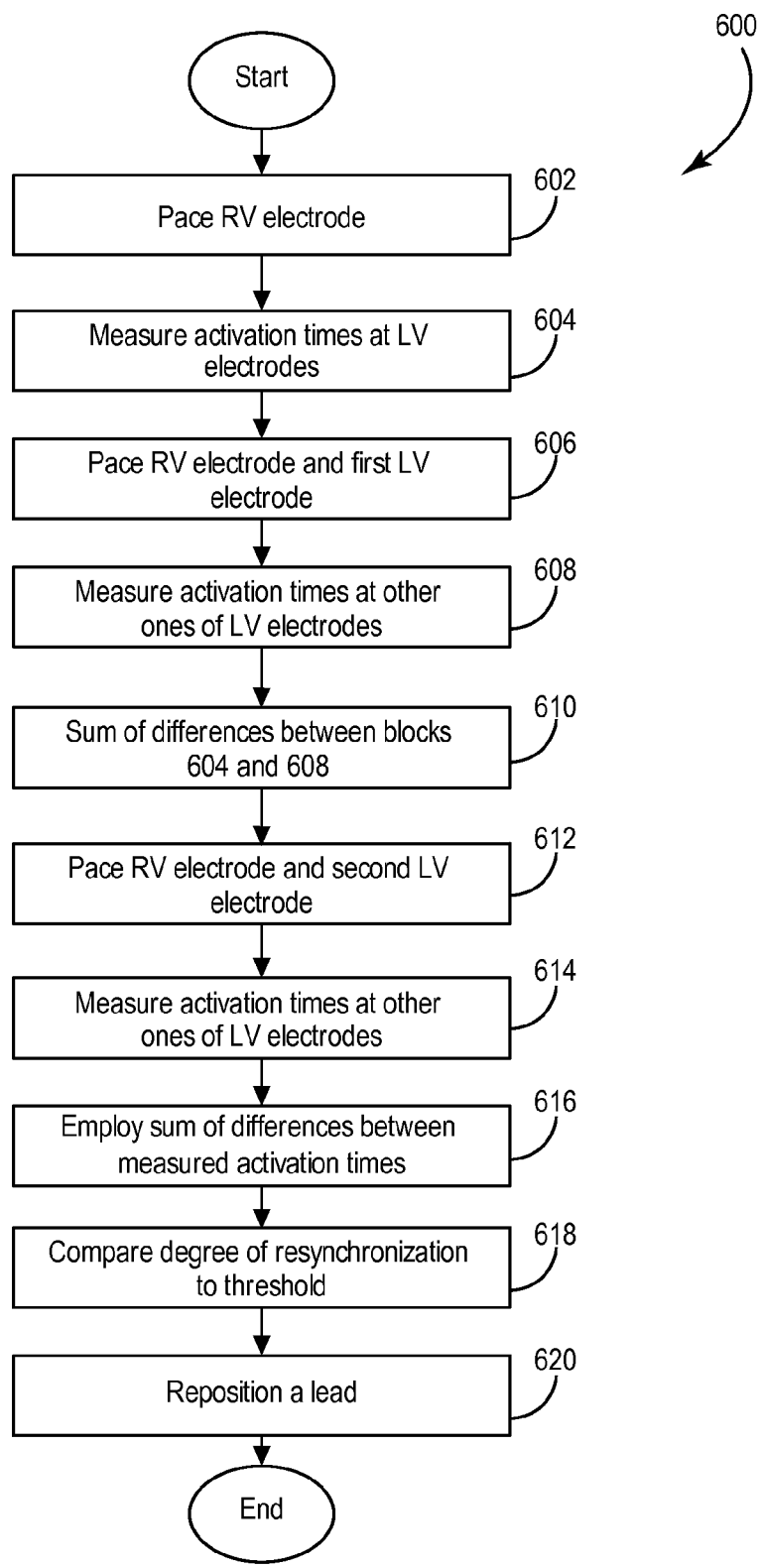
FIG. 8 is another general flow chart of an exemplary method that relies on a degree of resynchronization for determining whether the right ventricular lead and/or the left ventricular lead should be relocated.

FIG. 8 is a flow diagram that shows a method 600 performed to determine whether RV lead 18 and/or LV lead 20 should be repositioned. At block 602, activation times are sensed at the LV electrodes (e.g. LV1, LV2, LV3 and LV4) on lead 20 during RV only pacing or intrinsic rhythm. At block 604, activation times are measured at processor 80 and the activation time data is stored into memory 82. At block 606, a first biventricular pacing configuration is employed in which a RV electrode and a first one (e.g. LV1) of the plurality of LV electrodes are paced. At block 608, activation times at the non-pacing LV electrodes are measured. At block 610, a sum of differences between the measured activation times at blocks 604 and 608 to determine a first degree of resynchronization. In this particular case in which LV1 paces the LV, the degree of resynchronization is computed as follows:
(activation time at LV2 during RV only pacing−activation time at LV2 during biventricular pacing from RV electrode and LV1)+(activation time at LV3 during RV only pacing−activation time at LV3 during biventricular pacing from RV electrode and LV1)+(activation time at LV4 during RV only pacing−activation time at LV4 during biventricular pacing from RV electrode and LV1). The data generated by delivering pacing pulses from the RV and LV1 electrodes and the degree of resynchronization are stored into memory 82.

At block 612, a second biventricular pacing configuration is employed in which a RV electrode and a second one (e.g. LV2) of the plurality of LV electrodes are paced and the activation times are sensed at the non-pacing LV electrodes. At block 614, the activation times sensed at the non-pacing LV electrodes are measured at processor 80. At block 616, a sum of differences between the measured activation times at blocks 604 and 614 to determine a second degree of resynchronization. The second degree of resynchronization is calculated as follows:

(activation time at LV1 during RV only pacing−activation time at LV1 during biventricular pacing from RV electrode and LV2)+(activation time at LV3 during RV only pacing−activation time at LV3 during biventricular pacing from RV electrode and LV2)+(activation time at LV4 during RV only pacing−activation time at LV4 during biventricular pacing from RV electrode and LV2). The data generated by delivering pacing pulses from the RV and LV2 electrodes and the degree of resynchronization are stored into memory 82.

Blocks 612-616 are repeated for any remaining biventricular pacing configurations that have not been previously paced to determine, for example, the degree of resynchronizations for LV3 and LV4. For example, a third biventricular pacing configuration can be tested. The third biventricular pacing configuration includes the RV electrode and the LV3 that deliver pacing pulses to the RV and LV, respectively. The programmer, therefore, automatically switches from LV2 to LV3 to deliver the pacing pulses to the LV. After LV3 as the pacing electrode, pacing pulses are delivered to the RV and LV through the RV and LV3 electrodes, respectively. The electrical activation times for the LV1, LV2, and LV4 are measured and stored into memory 82.

The degree of resynchronization is then determined as follows:
(activation time at LV1 during RV only pacing−activation time at LV1 during biventricular pacing from RV electrode and LV3)+(activation time at LV2 during RV only pacing−activation time at LV2 during biventricular pacing from RV electrode and LV3)+(activation time at LV4 during RV only pacing−activation time at LV4 during biventricular pacing from RV electrode and LV3). The data generated by delivering pacing pulses through the RV and LV3 electrodes and the degree of resynchronization are stored into memory 82.

A fourth biventricular pacing configuration is then tested. The fourth biventricular pacing configuration includes the RV electrode and the LV4 that deliver pacing pulses to the RV and LV, respectively. The programmer 24 switches from LV3 to LV4 electrode to deliver the pacing pulses to the LV. After the programmer 24 has selected LV4 electrode, pacing pulses are delivered to the RV and LV through the RV and LV4 electrodes, respectively. The electrical activation times for the LV1, LV2, and LV3 are measured and stored into memory.

The degree of resynchronization is then determined as follows:
(activation time at LV1 during RV only pacing−activation time at LV1 during biventricular pacing from RV electrode and LV4)+(activation time at LV2 during RV only pacing−activation time at LV2 during biventricular pacing from RV electrode and LV4)+(activation time at LV3 during RV only pacing−activation time at LV3 during biventricular pacing from RV electrode and LV4). The data generated by delivering pacing pulses from the RV and LV4 electrodes and the degree of resynchronization are stored into memory.

After the resynchronization data has been obtained for each LV electrode (e.g. LV1, LV2, LV3, and LV4), then the resynchronization data is compared to a threshold (e.g. 60 ms) at block 618. At block 620, one of the RV lead and/or the LV lead 20 are repositioned if the degree of resynchronizations (e.g. first degree of resynchronization (also referred to as degree of resynchronization for LV1), second degree of resynchronization (also referred to as degree of resynchronization for LV2), third degree of resynchronization (also referred to as degree of resynchronization for LV3), and fourth degree of resynchronization of resynchronization (also referred to as degree of resynchronization for LV4) etc.) are less than a pre-determined threshold (e.g. 60 ms). In one or more embodiments, a simple criteria on the LV activation times during RV pacing or intrinsic rhythm can be used i.e., if the LV activation times are less than 60 ms, then move the lead or do not pace from that electrode. This simple criterion could be added to any of the above criteria for selecting a pacing vector.

The resynchronization index computed as a difference of activation times at electrodes during RV only pacing and biventricular pacing may be useful in identifying cases in which the multipolar LV lead 20 is in an area that is physically close to the RV pacing electrode. In such instances, very little improvement in resynchronization may be obtained with all biventricular pacing options from the LV lead 20 which may prompt the physician to reposition the RV lead 18 further away from the LV lead 20 and check whether sufficient improvement in resynchronization index is obtained. Thus, if the maximum value of resynchronization index among all biventricular pacing configuration is less than a certain predetermined threshold (e.g. 60 ms), none of the pacing LV electrodes are providing adequate resynchronization. If none of the LV electrodes are providing adequate resynchronization, then the RV lead 18 should be repositioned. After RV lead 18 has been repositioned, the operations outlined in FIG. 8 are rechecked to verify that the repositioned RV lead 18 and/or repositioned LV lead 20 offers better resynchronization.

While the invention has been described in its presently preferred form, it will be understood that the invention is capable of modification without departing from the spirit of the invention as set forth in the appended claims. For example, in one or more embodiments, two or more LV electrodes may be selected for multi-site pacing of the LV. An example of such a configuration may be seen with respect to U.S. Pat. No. 6,804,555 issued Oct. 12, 2004, and assigned to the assignee of the present invention, the disclosure of which is incorporated by reference in its entirety herein. Moreover, while the electrodes have been described as being able to either sense or pace, skilled artisans appreciate that other embodiments can employ electrodes that are able to both sense and pace. Additionally, many different medical electrical leads can be used to implement one or more embodiments. For example, St Jude's Quartet™ Quadripolar, left-ventricular pacing lead or Boston Scientific's EASYTRAK left ventricular pacing/sensing lead can be used.

The techniques described in this disclosure, including those attributed to the IMD 16, the programmer 24, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

Skilled artisans also appreciate that the exemplary methods presented in the flow diagrams are intended to illustrate the general functional operation of the devices described herein, and should not be construed as reflective of a specific form of software or hardware necessary to practice all of the methods described herein. It is believed that the particular form of software will be determined primarily by the particular system architecture employed in the device (e.g., IMD 16, programmer 24) and by the particular detection and therapy delivery methodologies employed by the device and/or system. Providing software and/or hardware to accomplish the described methods in the context of any modern IMD or programmer, given the disclosure herein, is within the abilities of one of skill in the art.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure. It is appreciated that the LV electrodes can be placed at locations about and/or along the LV. It is also appreciated that more than four LV electrodes can be used to monitor electrical activation times.

Furthermore, it is understood that degree of resynchronization is a function of multiple variables such as pacing electrode, A-V delay, and V-V delay. Optimization of degree of resynchronization is based on any one variable while keeping the other variables at a constant value. Additionally, other embodiments are contemplated in which a physician may optionally perform one or more operations for any methods described herein.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. For example, it is contemplated that other embodiments could use electrodes that are configured to pace and sense. Various modifications of the illustrative embodiments, as well as additional embodiments of the disclosure, will be apparent upon reference to this description.

What is claimed:

1. A method of cardiac pacing employing a right ventricular electrode and a plurality of left ventricular electrodes, comprising:
    a) pacing using the right ventricular electrode and measuring activation times at a plurality of the left ventricular electrodes;
    b) pacing using the right ventricular electrode and a first one of the left ventricular electrodes and measuring activation times at other ones of the left ventricular electrodes;
    c) computing a first degree of resynchronization based on a sum of differences of activation times in step a) and corresponding activation times in step b);
    d) pacing using the right ventricular electrode and a second one of the ventricular electrodes and measuring activation times at other ones of the left ventricular electrodes;
    e) computing a second degree of resynchronization based on the sum of differences of activation times in step a) and corresponding activation times in step d);
    f) determining whether the first and second degree of resynchronization are substantially similar; and
    g) in response to determining whether the first and second degree of resynchronization are substantially similar, selecting an optimal LV electrode from the first and second one of the ventricular electrodes using a non-degree of resynchronization factor.

2. The method of claim 1 wherein the non-degree of resynchronization factor comprises at least one of inadvertent phrenic nerve stimulation and depletion of a battery in an implantable medical device.

3. The method of claim 2 wherein the non-degree of resynchronization factor is prioritized.

* * * * *